US005690629A

United States Patent [19]
Asher et al.

[11] Patent Number: 5,690,629
[45] Date of Patent: Nov. 25, 1997

[54] APPARATUS FOR MAINTAINING VERTEBRAE OF A SPINAL COLUMN IN A DESIRED SPATIAL RELATIONSHIP

[75] Inventors: Marc A. Asher, Leawood, Kans.; Charles F. Heinig, Wareneck, Va.; William L. Carson, Columbia, Mo.; Walter E. Stripggen, Golden, Colo.; Terrence M. Stahurski, Seven Hills, Ohio

[73] Assignee: AcroMed Corporation, Cleveland, Ohio

[21] Appl. No.: 637,153

[22] Filed: Apr. 24, 1996

[51] Int. Cl.⁶ .................................................. A61B 17/70
[52] U.S. Cl. .................................. 606/61; 606/73; 606/75
[58] Field of Search .................................. 606/60, 61, 69, 606/70, 71, 72, 73, 75

[56] References Cited

U.S. PATENT DOCUMENTS

| | | |
|---|---|---|
| 4,047,524 | 9/1977 | Hall . |
| 5,084,049 | 1/1992 | Asher et al. . |
| 5,092,893 | 3/1992 | Smith . |
| 5,108,395 | 4/1992 | Laurain . |
| 5,129,899 | 7/1992 | Small et al. . |
| 5,261,910 | 11/1993 | Warden et al. . |
| 5,352,229 | 10/1994 | Goble et al. . |
| 5,395,372 | 3/1995 | Holt et al. . |

*Primary Examiner*—Michael Buiz
*Assistant Examiner*—David O. Reip
*Attorney, Agent, or Firm*—Tarolli, Sundheim, Covell, Tummino & Szabo

[57] ABSTRACT

An apparatus for use in retaining vertebrae of a spinal column in a desired spatial relationship includes a longitudinal member extendable along the spinal column. A fastener for connecting the longitudinal member to a vertebra includes a first end portion for engaging a vertebra and a second end portion connectable with the longitudinal member. A staple including a plurality of mounting projections for engaging the vertebra has surfaces for defining an opening through which the second end portion of the fastener extends. The staple includes surfaces for engaging the second end portion of the fastener to prevent relative rotation between the fastener and the staple.

18 Claims, 4 Drawing Sheets

APPARATUS FOR MAINTAINING VERTEBRAE OF A SPINAL COLUMN IN A DESIRED SPATIAL RELATIONSHIP

BACKGROUND OF THE INVENTION

The present invention relates to an apparatus for use inside the human body for maintaining vertebrae of a spinal column in a desired spatial relationship. More specifically, the present invention is directed to an apparatus to be fixed to an anterior portion of a spinal column for maintaining vertebrae of the spinal column in a desired spatial relationship.

U.S. Pat. No. 4,047,524 discloses a known apparatus that is anteriorly fixed to a spinal column for maintaining vertebrae of the spinal column in a desired spatial relationship. U.S. Pat. No. 4,047,524 discloses a staple having legs which attach to a vertebra of a spinal column. The staple includes a hole or holes through which screws extend that thread into the vertebra. The screws have heads through which cables are passed to retain the vertebrae in a desired spatial relationship. The staples are attached to the vertebrae and then the screws are threaded into the vertebrae so that the screws extend through the holes in the staples. Accordingly, the screws may rotate relative to the staple.

SUMMARY OF THE INVENTION

In accordance with the present invention, an apparatus for maintaining vertebrae of a spinal column in a desired spatial relationship includes a longitudinal member extendable along the spinal column. A fastener for connecting the longitudinal member to a vertebra includes a first end portion for attachment to the vertebra and a second end portion connectable with the longitudinal member. A staple has a plurality of mounting projections for attachment to the vertebra and surface means for defining an opening through which the second end portion of the fastener extends. The staple also includes means for engaging the second end portion of the fastener to prevent relative rotation between the fastener and the staple. In a first embodiment of the present invention projections on the staple only engage parallel side surfaces of the second end portion of the fastener. In a second embodiment of the present invention, projections on the staple engage parallel side surfaces and transverse side surfaces of the second end portion of the fastener.

BRIEF DESCRIPTION OF THE DRAWINGS

The foregoing and other features of the present invention will become apparent to one skilled in the art upon consideration of the following description of the preferred embodiments of the invention with reference to the accompanying drawings, wherein.

DESCRIPTION OF A PREFERRED EMBODIMENT OF THE INVENTION

Figure 1:
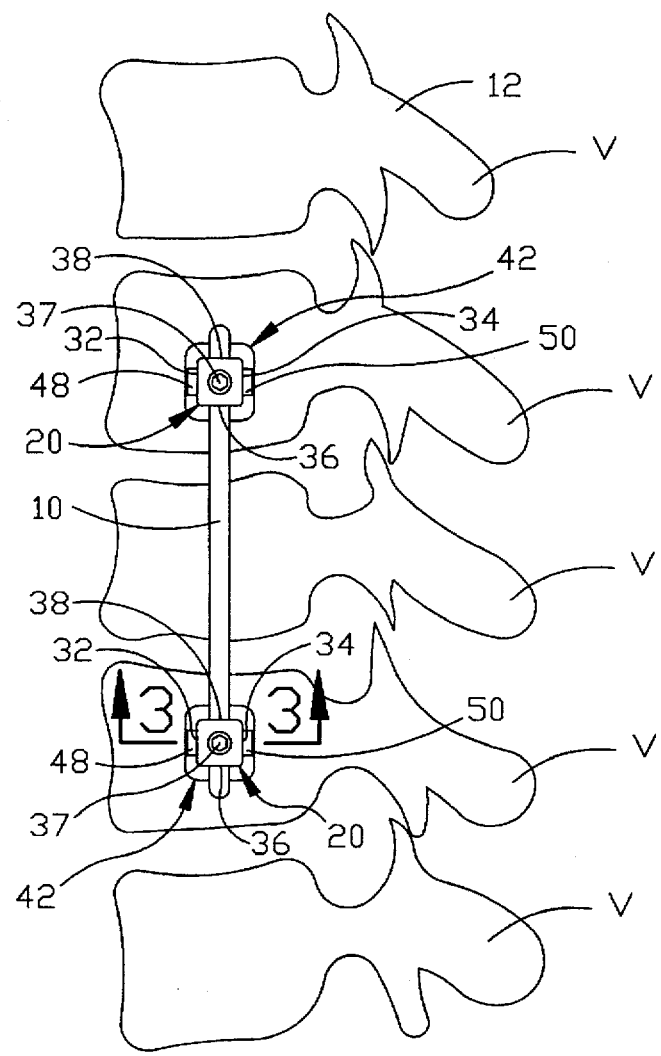
FIG. 1 is a left lateral view of a human spinal column in which an apparatus constructed in accordance with a first embodiment of the present invention has been applied.

A surgically implantable longitudinal rod 10 (FIG. 1) for maintaining vertebrae of a spinal column in a desired spatial relationship is connected inside a human body to anterior portions of vertebrae V of a spinal column 12 by fasteners 20. The rod 10 can be contoured to conform to any desired curvature of the spinal column 12. The rod 10 has a length which is at least sufficient to enable the rod to span at least two vertebrae V. In the embodiment of the invention illustrated in FIG. 1, the rod 10 spans three vertebrae V. Of course, the length of the rod in any particular installation will depend upon the condition to be corrected, the size of the patient's vertebrae, and the number of vertebrae V to be held in a desired spatial relationship by the rod.

Figure 2:
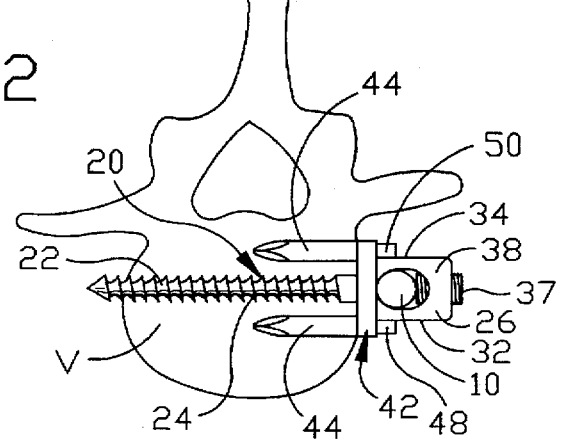
FIG. 2 is a top view of a vertebra showing the location of the apparatus in FIG. 1 on the vertebra.
Figure 3:
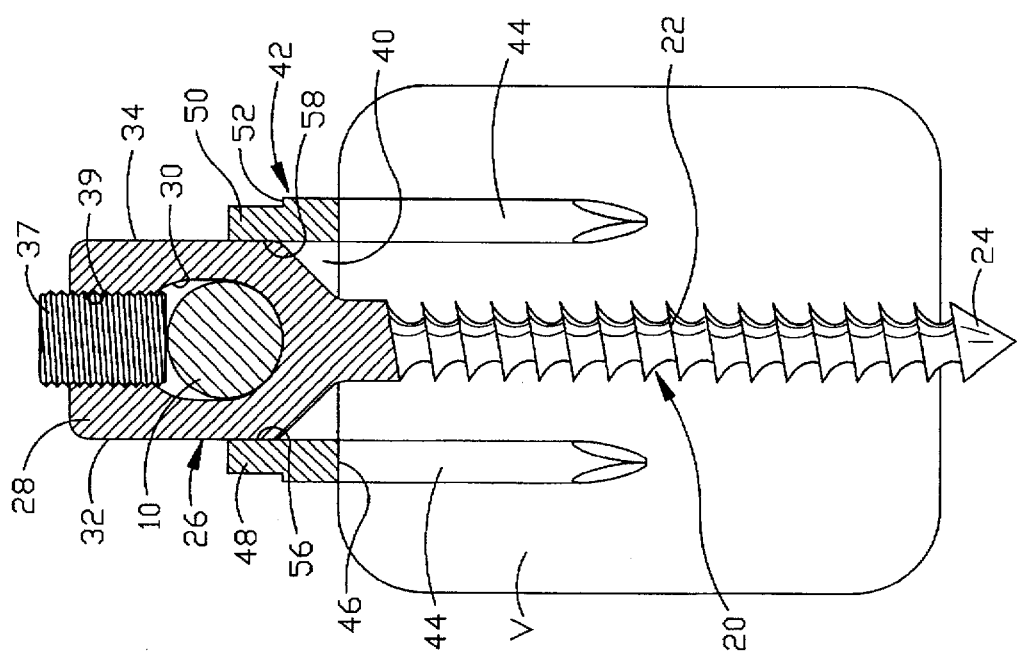
FIG. 3 is an enlarged sectional view, taken generally along the line 3—3 of FIG. 1.

The rod 10 is connected to respective vertebrae V by fasteners 20 (FIGS. 2 and 3) made of a suitable biocompatible material, such as titanium or stainless steel. Each of the fasteners 20 has a threaded inner end portion 22 having a coarse helical thread convolution 24 which engages the vertebra V. An outer end portion 26 of the fastener 20 includes a block portion 28 (FIG. 3) with an opening 30 through which the rod 10 extends. Preferably, the block portion 28 is square-shaped in plan view (FIG. 1) and includes parallel side surfaces 32 and 34 that extend parallel to the longitudinal rod 10. Transverse side surfaces 36 and 38 extend parallel to each other, transverse to the parallel side surfaces 32 and 34, and transverse to the rod 10.

Preferably, the opening 30 in the block portion 28 includes a pair of axially spaced arcuate surfaces (not shown). The pair of axially spaced arcuate surfaces engage portions of the rod 10 at axially spaced locations. Reference is hereby made to U.S. Pat. No. 5,024,213 to Asher et al. and assigned to the same assignee as the present invention. U.S. Pat. No. 5,024,213 describes the arcuate surfaces and their function in greater detail. A set screw 37 threadably engages an opening 39 in the block portion 28 to press the longitudinal rod 10 against the arcuate surfaces of the opening 30.

Figure 4:
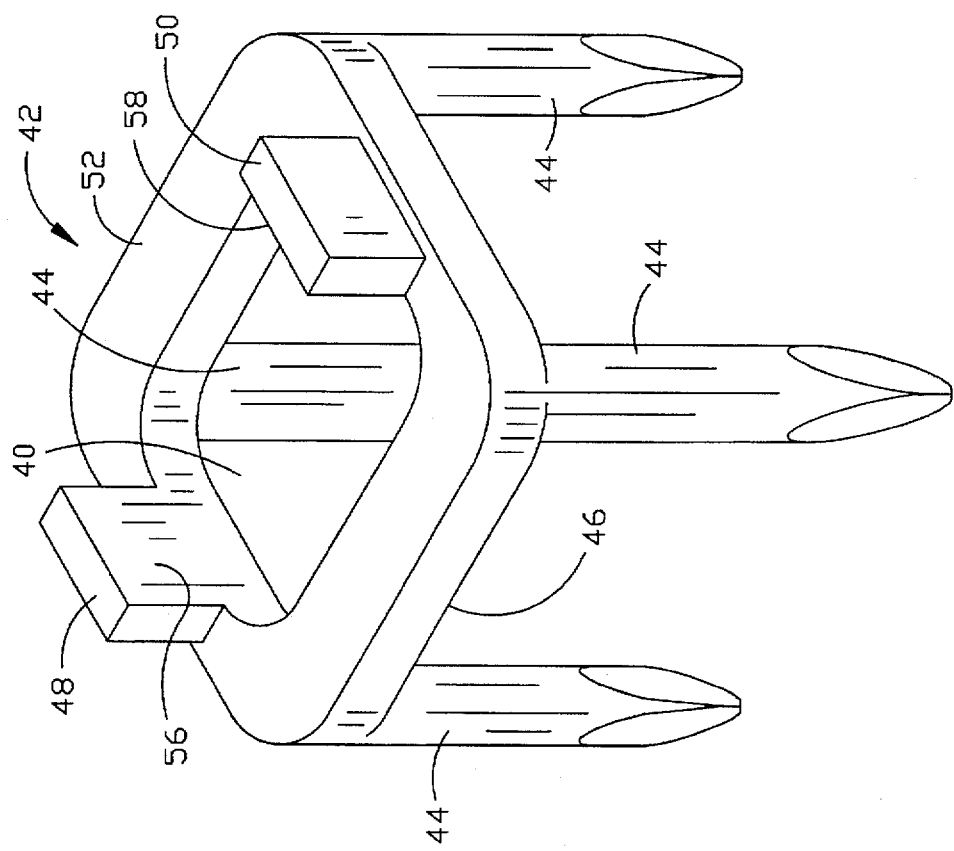
FIG. 4 is an enlarged pictorial view of a first embodiment of a staple which is a part of the apparatus of FIG. 1.

The block portion 28 of the fastener 20 extends through an opening 40 in a first embodiment of a staple 42 (FIGS. 3 and 4) made of a suitable biocompatible material, such as stainless steel or titanium. The opening 40 is shaped to correspond to the shape of the block portion 28 and is therefore, preferably square-shaped. The staple 42 includes a plurality of mounting projections 44, preferably four, for attachment to the vertebra V.

Preferably, the projections 44 are pointed to penetrate a vertebra. However, the projections 44 may have any desired shape that permits attachment of the staple 42 with a vertebra. The projections 44 extend from a side surface 46 of the staple 42. The side surface 46 engages the vertebra V when the staple 42 is mounted to a vertebra.

A pair of projections 48 and 50 extend from a side surface 52 of the staple opposite from the side surface 46. The projections 48 and 50 are located on opposite sides of the opening 40. The projection 48 includes a side surface 56 and the projection 50 includes a side surface 58 extending parallel to the side surface 56. The side surfaces 56 and 58 define a portion of the opening 40 in the staple 42 and engage the parallel side surfaces 32 and 34 of the block portion 28.

When the rod 10 is to be mounted on a spinal column 12, a plurality of fasteners 20 are connected to the anterior portions of the vertebrae V. Staples 42 are placed over the fasteners 20 with the projections 48 and 50 engaging the parallel side surfaces 32 and 34 of the block portions 28. Force is applied to the staples 42 to cause the projections 44 to penetrate into the vertebrae and become attached to the vertebrae.

After the rod 10 has been contoured to the desired configuration, if needed, the rod 10 is placed through the openings 30 in the fasteners 20. Once the rod 10 has been positioned relative to the fasteners 20 and the staples 42, the set screws 37 are tightened to clamp the rod 10 in the openings 30 of the fasteners 20. The engagement of the parallel side surfaces 32 and 34 of the block portion 28 by the projections 48 and 50 prevents relative movement between the fastener 20, rod 10, and the staple 42.

Figure 6:
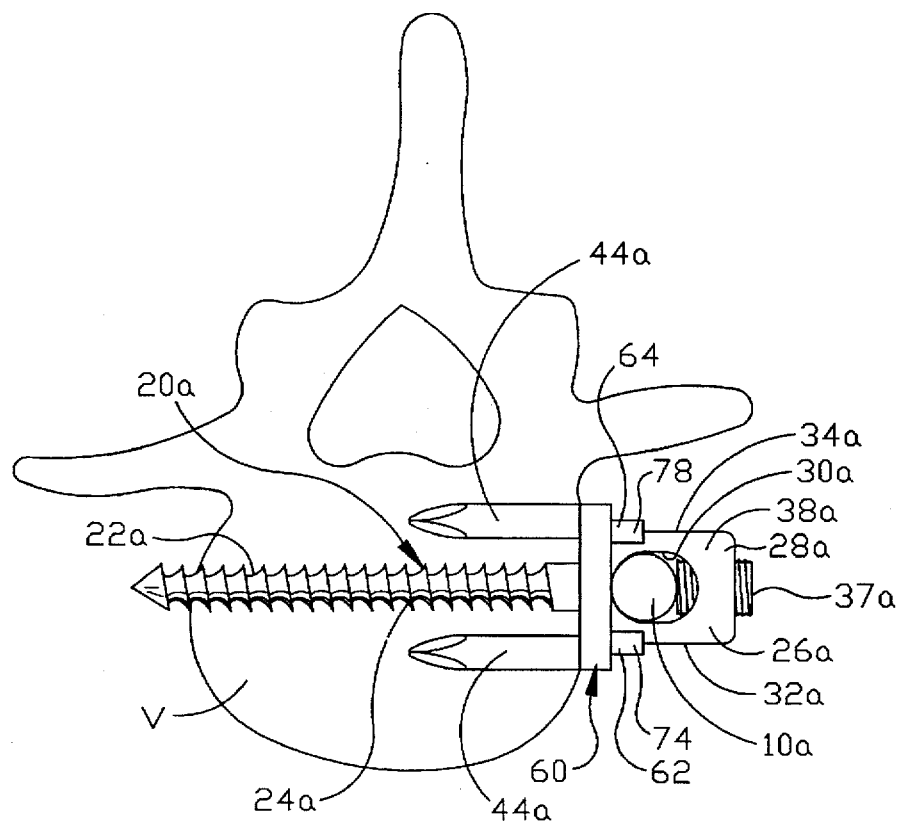
FIG. 6 is a top view of a vertebra showing the location of the apparatus in FIG. 5 on the vertebra.
Figure 7:
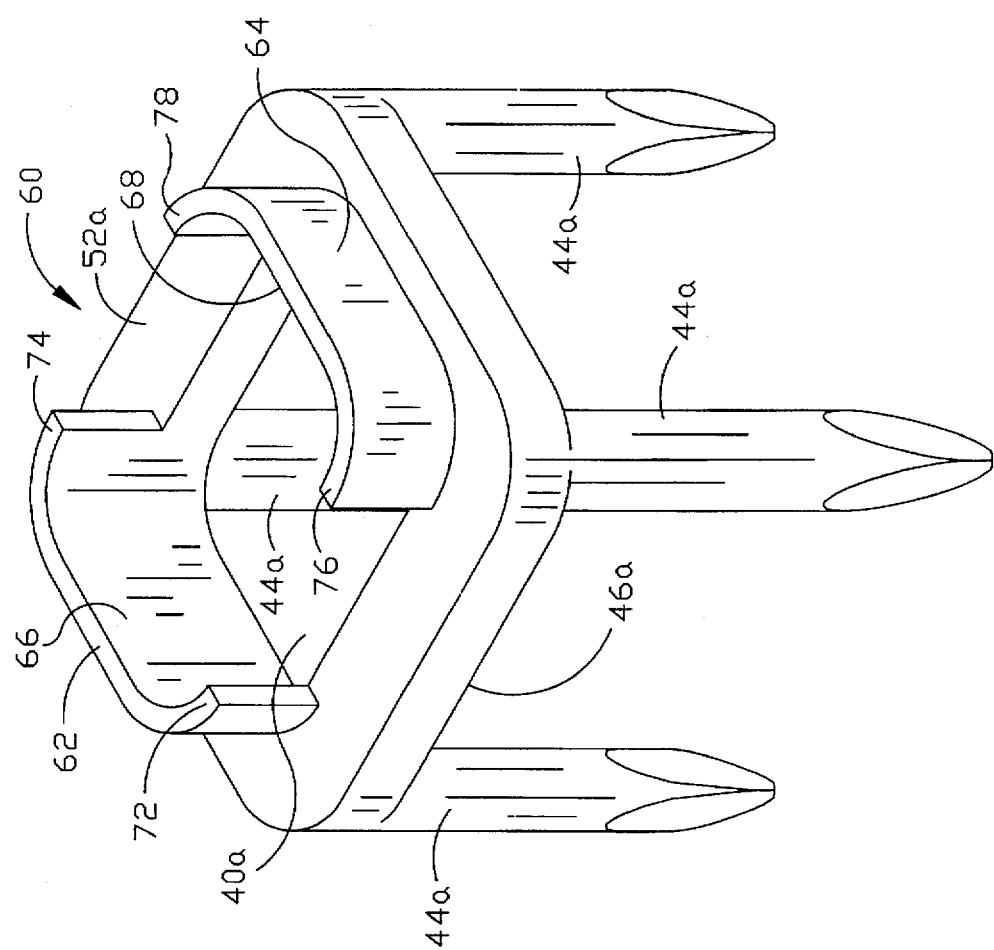
FIG. 7 is an enlarged pictorial view of a second embodiment of a staple which is part of the apparatus of FIG. 5.

In the embodiment of the invention illustrated in FIGS. 1–4, the projections 48 and 50 of the staple 42 only engage the parallel side surfaces 32 and 34 of the fastener 20. In the embodiment of the invention illustrated in FIGS. 5–7, the staple includes projections that engage the parallel side surfaces of the block portion and the transverse side surfaces of the block portion. Since the embodiment of the invention illustrated in FIGS. 5–7 is generally similar to the embodiment of the invention illustrated in FIGS. 1–4, similar numerals will be utilized to designate similar components, the suffix letter "a" being associated with the numerals of FIGS. 5–7 to avoid confusion.

Figure 5:
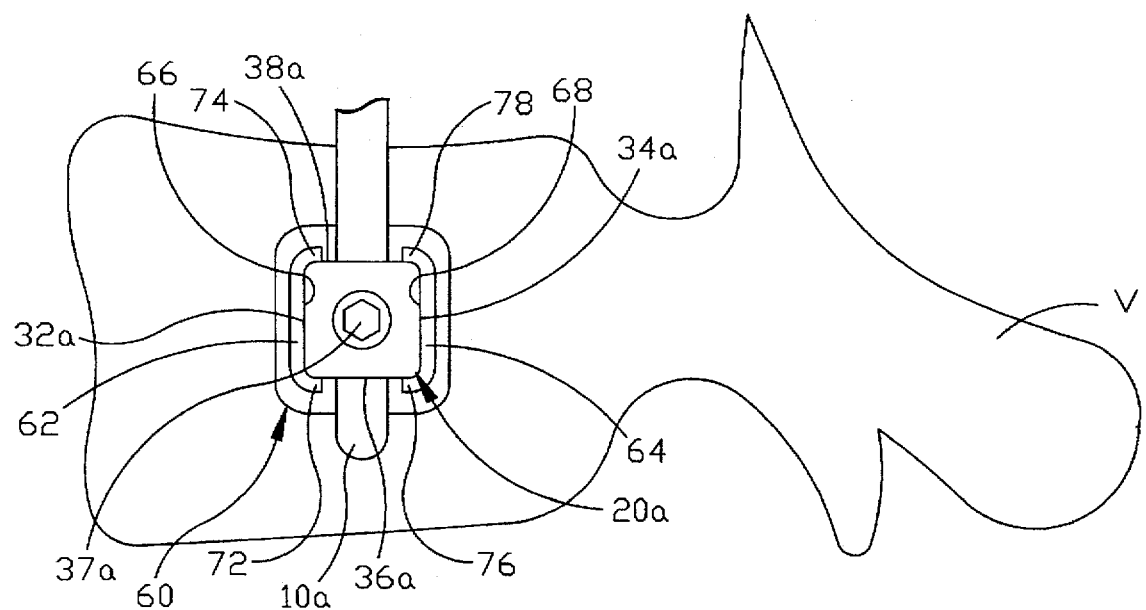
FIG. 5 is an enlarged left lateral view of a human spinal column in which an apparatus constructed in accordance with a second embodiment of the present invention has been applied.

A surgically implantable longitudinal rod 10a, a portion of which is shown in FIG. 5, for maintaining vertebrae of a spinal column in a desired spatial relationship is connected inside a human body to anterior portions of vertebrae V of a spinal column by fasteners 20a, only one of which is shown in FIG. 5. The fastener 20a is made of a suitable biocompatible material, such as titanium or stainless steel. The fastener 20a has a threaded inner end portion 22a (FIG. 6) having a coarse helical thread convolution 24a which engages the vertebra V.

An outer end portion 26a of the fastener 20a includes a block portion 28a (FIG. 6) with an opening 30a through which the rod 10a extends. Preferably, the block portion 28a is square-shaped in plan view (FIG. 5) and includes parallel side surfaces 32a and 34a that extend parallel to the longitudinal rod 10a. Transverse side surfaces 36a and 38a extend parallel to each other, transverse to the parallel side surfaces 32a and 34a, and transverse to the rod 10a. A set screw 37a threadably engages an opening in the block portion 28a to press the longitudinal rod 10a against the surfaces of the opening 30a.

The block portion 28a of the fastener 20a extends through an opening 40a (FIG. 7) in a second embodiment of a staple 60 made of a suitable biocompatible material, such as stainless steel or titanium. The opening 40a is shaped to correspond to the shape of the block portion 28a and is therefore, preferably square-shaped. The staple 60 includes a plurality of mounting projections 44a, preferably four, for attachment to the vertebrae V.

The projections 44a may have any desired shape that permits attachment of the staple 60 with a vertebra. The projections 44a extend from a side surface 46a of the staple 60. The side surface 46a engages the vertebra V when the staple 60 is mounted to a vertebra.

A pair of projections 62 and 64 extend from a side surface 52a of the staple opposite from the side surface 46a. The projections 62 and 64 are located on opposite sides of the opening 40a. The projections 62 and 64 extend along a side of the opening 40a and around the corners of the opening. The projection 62 includes a side surface 66 and the projection 64 includes a side surface 68 extending parallel to the side surface 66. The side surfaces 66 and 68 define a portion of the opening 40a in the staple 60 and engage the parallel side surfaces 32a and 34a of the block portion 28a (FIG. 5).

The projection 62 includes end portions 72 and 74 that extend around the corners of the opening 40a and are engageable with transverse side surfaces 36a and 38a of the block portion 28a. The projection 64 includes end portions 76 and 78 that extend around the corners of the opening 40a and are engageable with the transverse side surfaces 36a and 38a of the block portion 28a. The end portions 72, 74 and 76, 78 of the projections 62 and 64 help prevent rotation of the fastener 20a relative to the staple 60.

When the rod 10a is to be mounted on a spinal column, a plurality of fasteners 20a are connected to the anterior portions of the vertebrae. Staples 60 are placed over the fasteners 20a with the side surfaces 66 and 68 of the projections 62 and 64 engaging the parallel side surfaces 32a and 34a of the block portions 28a, the end portions 72 and 76 of the projections engaging the transverse side surfaces 36a, and the end portions 74 and 78 of the projections 62 and 64 engaging the transverse side surfaces 38a. The rod 10a is placed through the openings 30a in the fasteners 20a and the set screws 37a are tightened to clamp the rod 10a in the openings 30a. The engagement of the projections 62 and 64 with the parallel side surfaces 32a and 34a and the transverse side surfaces 36a and 38a prevents relative movement between the fasteners 20a, rod 10a, and the staples 60.

From the above description of the invention, those skilled in the art will perceive improvements, changes and modifications. Such improvements, changes and modifications within the skill of the art are intended to be covered by the appended claims.

Having described the invention, the following is claimed:

1. An apparatus for use in retaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion connectable with said longitudinal member; and a staple including a plurality of mounting projections for attachment to the vertebra, said mounting projections extending from a first side surface of said staple, said staple further including surface means for defining an opening through which said second end portion of said fastener extends, said staple including means for engaging said second end portion of said fastener to prevent relative rotation between said fastener and said staple, wherein said means for engaging said second end potion of said fastener includes said surface means for defining said opening in said staple.

2. An apparatus as set forth in claim 1 wherein said surface means defining said opening in said staple is engageable with side surfaces of said second end portion of said fastener.

3. An apparatus as set forth in claim 2 wherein said surface means defining said opening in said staple includes parallel side surfaces engageable with parallel side surfaces of said second end portion of said fastener.

4. An apparatus as set forth in claim 3 wherein said second end portion of said fastener includes transverse side surfaces extending transverse to said parallel side surfaces and said longitudinal member, said surface means defining said opening in said staple being engageable with said transverse side surfaces of said second end portion of said fastener.

5. An apparatus for use in retaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion connectable with said longitudinal member; and a staple including a plurality of mounting projections for attachment to the vertebra, said mounting projections extending from a first side surface of said staple, said staple further including surface means for defining an opening through which said second end portion of said fastener extends, said staple including means for engaging said second end portion of said fastener to prevent relative rotation between said fastener and said staple, said means for engaging said second end portion of said fastener including surface means for defining said opening in said staple and a first projection engageable with said second end portion of said fastener extending from a second side surface of said staple opposite from said first side surface of said staple from which said plurality of mounting projections extend.

6. An apparatus as set forth in claim 5 wherein said means for engaging said second end portion of said fastener includes a second projection engageable with said second end portion of said fastener extending from said second side surface of said staple.

7. An apparatus as set forth in claim 6 wherein said second end portion of said fastener includes a block portion having side surfaces and an opening through which said longitudinal member is extendable, each of said first and second projections extending from said second side surface of said staple includes a side surface engageable with one of said side surfaces of said block portion of said fastener and defining said opening in said staple.

8. An apparatus as set forth in claim 7 wherein said side surfaces on said block portion are parallel and said side surface of said first projection is parallel to said side surface of said second projection.

9. An apparatus as set forth in claim 8 wherein said block portion includes transverse side surfaces extending transverse to said parallel side surfaces and said longitudinal member, each of said first and second projections extending from said second side surface of said staple including portions engageable with each of said transverse side surfaces.

10. An apparatus as set forth in claim 8 wherein said first and second projections are located on opposite sides of said opening in said staple, said longitudinal member being extendable between said first and second projections.

11. An apparatus as set forth in claim 8 wherein said fastener includes a set screw threadably engageable with said block portion for clamping said longitudinal member in said opening in said block portion.

12. An apparatus for use in retaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion connectable with said longitudinal member; and a staple including a plurality of mounting projections for attachment to the vertebra, said mounting projections extending from a first side surface of said staple, said staple further including surface means for defining an opening through which said second end portion of said fastener extends, said staple including means for engaging said second end portion of said fastener to prevent relative rotation between said fastener and said staple, said means for engaging said second end portion of said fastener including a first projection engageable with said second end portion of said fastener extending from a second side surface of said staple opposite from said first side surface of said staple from which said plurality of mounting projections extend.

13. An apparatus as set forth in claim 12 wherein said means for engaging said second end portion of said fastener includes a second projection engageable with said second end portion of said fastener extending from said second side surface of said staple.

14. An apparatus as set forth in claim 13 wherein said first projection extending from said second side surface of said staple includes a side surface engageable with a side surface of said second end portion of said fastener, said second projection including a side surface extending parallel to said side surface of said first projection and engageable with said second end portion of said fastener.

15. An apparatus as set forth in claim 14 wherein said first projection is located on a first side of said opening in said staple and said second projection is located on a second side of said opening in said staple opposite from said first side of said opening.

16. An apparatus as set forth in claim 14 wherein said second end portion of said fastener includes parallel side surfaces engageable with said parallel side surfaces of said first and second projections and transverse side surfaces extending transverse to said parallel side surfaces, each of said first and second projections including portions engageable with said transverse side surfaces of said second end portion.

17. An apparatus as set forth in claim 14 wherein said side surfaces of said first and second projections extending from said second side surface of said staple define said opening in said staple.

18. An apparatus as set forth in claim 14 wherein said second end portion of said fastener includes a block portion having an opening through which said longitudinal member is extendable, said block portion including parallel side surfaces extending parallel to said side surfaces of said first and second projections of said staple and engageable with said side surfaces of said first and second projections.

* * * * *